US006350338B1

(12) United States Patent
Comiskey et al.

(10) Patent No.: US 6,350,338 B1
(45) Date of Patent: Feb. 26, 2002

(54) REFLECTED LIGHT GLARE MINIMIZATION FOR ATHLETIC CONTEST

(75) Inventors: Stephen W. Comiskey, 3387 Stephenson Pl., NW., Washington, DC (US) 20015; Barrett O. Comiskey, Cambridge, MA (US)

(73) Assignee: Stephen W. Comiskey, Washington, DC (US)

( * ) Notice: Subject to any disclaimer, the term of this patent is extended or adjusted under 35 U.S.C. 154(b) by 0 days.

(21) Appl. No.: 09/521,856

(22) Filed: Mar. 9, 2000

Related U.S. Application Data

(63) Continuation of application No. 09/217,074, filed on Dec. 21, 1998, now Pat. No. 6,096,154, which is a continuation of application No. 08/240,895, filed on May 11, 1994, now Pat. No. 5,939,142.

(51) Int. Cl.[7] .......................... B44C 1/165; B41M 3/12; A61F 9/00

(52) U.S. Cl. ....................... 156/230; 156/240; 156/247; 427/1; 427/147; 428/195; 132/319; 2/206; 128/858

(58) Field of Search ................................ 156/230, 240, 156/241, 247, 277, 289, 248; 427/1, 146, 147; 428/195, 199, 211, 914; 128/201.18, 858; 132/216, 319; 2/206

(56) References Cited

U.S. PATENT DOCUMENTS

| | | | | | |
|---|---|---|---|---|---|
| 1,761,664 | A | | 6/1930 | Harris | |
| 1,850,540 | A | * | 3/1932 | Erickson | 132/216 |
| 2,033,139 | A | | 3/1936 | Jefferis | |
| 2,842,142 | A | * | 7/1958 | Peck | 132/216 |
| 2,851,805 | A | | 9/1958 | Allen | |
| 3,594,813 | A | | 7/1971 | Sanderson | |
| 4,285,338 | A | | 8/1981 | Lemelson | |
| 4,719,909 | A | * | 1/1988 | Micchia et al. | 128/156 |
| 4,745,916 | A | * | 5/1988 | Seber | 128/155 |
| 4,979,811 | A | | 12/1990 | Boyer | |
| 5,052,418 | A | | 10/1991 | Miller | |
| 5,592,687 | A | * | 1/1997 | Lajeunesse | 2/9 |
| 5,609,150 | A | * | 3/1997 | Maged | 128/201.18 |
| 5,718,224 | A | * | 2/1998 | Muchin | 128/200.24 |
| 6,096,154 | A | * | 8/2000 | Comiskey et al. | 156/230 |
| D434,524 | S | * | 11/2000 | Kalfsky et al. | D28/4 |
| D441,081 | S | * | 4/2001 | Mueller | D24/189 |

OTHER PUBLICATIONS

Pleadings for Civil Action No. 00–1993–A in the United States District Court for the Eastern District of Virginia (Alexandria Division) (with Tabs 1–48).

Pleadings from Case No. 01–1141 in the United States District Court of Appeals for the Federal Circuit (with Tabs 1–17).

* cited by examiner

*Primary Examiner*—Richard Crispino
*Assistant Examiner*—J. A. Lorengo
(74) *Attorney, Agent, or Firm*—Hunton & Williams

(57) ABSTRACT

A method and product for reducing reflected light glare into a human's eyes from the human's cheeks while simultaneously providing a non-verbal communication to others is provided, especially for use by participants in athletic contests. Underneath the human's eyes on the cheeks at a reflective location on the cheeks at which incident direct or indirect light is likely to be reflected into a human's eyes a non-toxic, non-reflective colored and finished material in the form of a predefined clearly demarcated geometric shape is applied. Within a week after the application (typically within less than a few hours after the athletic contest is over) the non-reflective material is removed. The non-reflective material may comprise eye black, applied using a stencil, or it may comprise a temporary tattoo or decal, applied in the conventional manner. The shape preferably is a sports apparel or equipment manufacturer's or distributor's logo and/or letters, or a team name, mascot or logo. The material is preferably black or dark colored, and any non-black or non-dark colored portions providing demarcation between elements of the shape comprises a dull or matte color having a wavelength of greater than about 650 nm and less than about 470 nm.

12 Claims, 3 Drawing Sheets

REFLECTED LIGHT GLARE MINIMIZATION FOR ATHLETIC CONTEST

This application is a continuation of U.S. patent application Ser. No. 09/217,074, filed on Dec. 21, 1998, now U.S. Pat. No. 6,096,154 which is a continuation of U.S. patent application Ser. No. 08/240,895 filed May 11, 1994, now U.S. Pat. No. 5,939,142.

BACKGROUND AND SUMMARY OF THE INVENTION

Participants in athletic contests, particularly participants in team sports such as football, soccer, baseball, and lacrosse, that are played outside during the day, or in well lit stadiums, minimize the light that is reflected from their cheeks into their eyes by applying conventional eye black to their cheeks. Conventional eye black typically includes as ingredients Vaseline, lanolin, ceresin wax, beeswax, carnauba wax, and black oxide of iron C177499UV. Eye black may be applied with a finger by dipping it into a large container and wiping on the cheeks under the eye, or applied with a marker in much the same form that lipstick is applied.

In the promotion of sports apparel and equipment by apparel or equipment manufacturers or distributors, there is intense competition and one of the major ways that such companies promote their products is by having their products used by participants in high visibility athletic contests, especially those that are televised. For example the larger shoe manufacturers in the world have millions of dollars of endorsement contracts with teams, sports leagues, and individual players to promote their products through players wearing equipment such as shoes, shirts, wrist bands, or the like, having the logo of the manufacturer or distributor thereon.

Another product market area also usually associated with athletics, but also used for other purposes, are the supply and sale of decals or temporary tattoos having team names, logos, mascots, slogans, and the like. The decals and temporary tattoos are made to be bright and/or reflective and can be applied on different parts of the body, although the manufacturers often caution against applying them near the eyes or on sensitive skin, often because the products are widely used by children.

According to the present invention, a method and products are provided which utilize and simulate concepts from each of the three heretofore distinct art areas described above, providing a method and product by which participants in athletic contests can accomplish the functional task of reducing reflected light glare into their eyes while at the same time advertising a sports apparel or equipment manufacturer's or distributor's logo and/or name, or providing a like non-verbal communication to others. According to the present invention eye black, or temporary tattoos or decals having basically the same non-reflective properties as eye black, are applied underneath the eyes in the form of a predefined clearly demarcated geometric shape which provides a non-verbal communication to others. Unlike conventional temporary tattoos and decals, the geometric shape according to the invention is non-reflective, typically as a dull or matte black or other dark color having a wavelength greater than about 690 nm and less than about 430 nm. It is non-reflective in the sense that it reflects very little light from the visible spectrum and, therefore, appears dull or matte. Unlike conventional eye black, the material is applied in a clearly demarcated shape which—rather than being a blob or streak, provides a non-verbal communication to others, such as an advertisement for a sports apparel or equipment manufacturer or distributor or a team name, mascot or logo.

According to one aspect of the present invention, a method of reducing reflective light glare into a human's eyes from the human's cheeks while simultaneously providing a non-verbal communication to others is provided. The method comprises the steps of: (a) Applying underneath the human's eyes, on the human's cheeks, generally covering a reflective location on the cheeks, at which incident direct or indirect light is likely to be reflected into the human's eyes, a non-toxic material having a non-reflective colored and finished exterior in the form of a predefined clearly demarcated geometric and predefined shape which provides a non-verbal communication to others. And, (b) within a week after application of the non-reflective material from step (a), removing it. Typically the human is a participant in an athletic contest, in which case step (a) is practiced within a few hours or less before the start of the athletic contest and so that the material substantially eliminates reflection of incident direct or indirect light off the participant's cheeks into the participant's eyes, and step (b) is practiced within a few hours or less after the athletic contest is over.

Steps (a) and (b) as set forth above may be practiced in a number of different ways. According to one particular aspect of the invention, step (a) is practiced by placing a stencil underneath one of the human's eyes and over the reflective location on a cheek, the stencil having a cutout of the clearly demarcated geometric and predefined shape, and then applying eye black to the cheek reflective location under the cutout, and then removing the stencil; and wherein step (b) is practiced by wiping off the eye black, or washing it off with soap and water, or both wiping it off and washing it off. Step (a) further may be practiced by repeating the steps of claim 3 for the other of the human's eyes.

According to another aspect of the invention, the material is a decal comprising a substrate, having top and bottom faces, the top face of the decal being the non-reflective material, and the bottom face of the decal having a pressure sensitive adhesive thereon; and in which case step (a) is practiced by applying the bottom face of the decal to the reflective cheek portion and pressing so that the adhesive holds the decal in place.

According to yet another aspect of the invention, the material is a temporary tattoo, provided on a backing, the temporary tattoo provided on a top face of the backing and illustrating the reverse of the clearly demarcated geometric and predefined shape, and the backing having a bottom face; and in which case step (a) is practiced by cleaning a cheek where the temporary tattoo is to be applied, putting the temporary tattoo on the top face of the backing on the reflective location of the human's cheek to which it is to be applied, wetting the bottom face of the backing with water and pressing it into contact with the cheek for sufficient time for the temporary tattoo to adhere to the cheek, and sliding off the backing from the temporary tattoo. Step (b) is typically practiced by rubbing the temporary tattoo off using alcohol or baby oil, or applying tape thereto and then pulling off the tape.

Regardless of the details of practicing the invention as described above, step (a) is preferably practiced to provide as the clearly demarcated geometric and predefined shape a sports apparel or equipment manufacturer's or distributor's logo, the logo having a size complying with regulations of a regulatory body which oversees the athletic contest. Further, the geometric shape may include letters instead of or in addition to the logo, with a primarily black or dark colored area sized to comply with the regulatory body's standards and with the letters or any demarcation between any letters in the primarily black or dark colored area comprising a dull or matte color and absorbing most of the light in the visible spectrum. Alternatively the clearly demarcated geometric and predefined shape may comprise a representation of a sports team name, mascot or logo. In some cases the logo (whether commercial or sports team) may have a directional bias and step (a) of the method described above may be practiced by applying the logo with the correct directional bias under one of the human's eyes, and with the reverse of the correct directional bias under the other of the human's eyes; or the logo may have the correct directional bias under both the human's eyes.

According to another aspect of the present invention a decal or temporary tattoo having a clearly demarcated geometric and predefined shape and dimensioned to substantially cover the area on a human's cheek underneath one of the human's eyes is provided. The decal or temporary tattoo comprises: A clearly demarcated geometric and predefined shape dimensioned to substantially cover the area of a reflective location on a human's cheek at which incident direct or indirect light is likely to be reflected into the human's eye, the temporary tattoo or decal being non-toxic and having an exterior, when applied, surface of non-reflective colored and finished material sufficient to substantially eliminate the reflection of incident direct or indirect light off the human's cheek into the human's eye. Desirably, the clearly demarcated geometric and predefined shape is a sports apparel or equipment manufacturer's or distributor's logo and/or letters identifying the manufacturer or distributor, no part of the shape that is not a dull or matte dark color having a size significant enough to allow significant reflection of incident direct or indirect light off the human's cheeks into the human's eyes. For example, the clearly demarcated geometric and predefined shape may consist of a sports apparel or equipment manufacturer's or distributor's logo and/or letters, and a clearly demarcated shape will have a size complying with the regulations of any regulatory body which oversees the participants in an athletic contest by whom the decal or temporary tattoo is utilized.

According to yet another aspect of the present invention an eye black clearly demarcated geometric and predefined shape is provided produced according to the method as described above x-herein a particular design is stenciled under a user's eyes using eye black.

It is the primary object of the present invention to provide a method and apparatus for simultaneously reducing reflective light glare into a human's eyes from the human's cheeks while simultaneously, providing a nonverbal communication to others in a simple and effective manner, particularly one that lends itself to commercial advertisement or sports team promotion. This and other objects of the invention will become clear from an inspection of the detailed description of the invention, and from the appended claims.

DETAILED DESCRIPTION OF THE DRAWINGS

Figure 1:
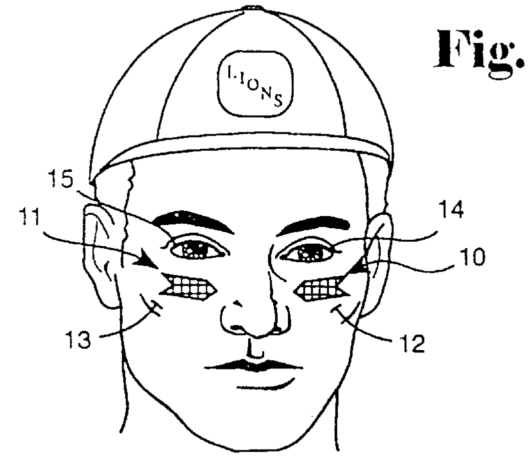
FIG. 1 is a front schematic view of an athletic contest participant having non-reflective material applied under his or her eyes in a clearly demarcated geometric and predefined shape in accordance with the present invention.

FIG. 1 schematically illustrates clearly demarcated geometric and predefined shapes 10 and 11 according to the present invention which are applied to generally cover a reflective location on each of the cheeks 12, 13 of a human, such as a participant in an athletic contest. The reflective locations on the cheeks 12, 13 are those at which incident direct or indirect light is likely to be reflected into the human's eyes 14, 15. The shapes 10, 11 are applied at the same location that conventional eye black is applied. This location is not scientifically precise or uniform from person to person since it may depend upon the person's facial contours, but for most participants in outdoor or brightly lighted athletic facilities, particularly participants in team sports using a ball (such as football, soccer, baseball, lacrosse, etc.), it is applied about one-quarter to three-quarters of an inch under the participant's eyes (e.g. starting at the bottom of the eye socket) and continuing downwardly about a half inch to an inch, and extending in width generally the width of the eye 14 or 15 (or slightly more or less). In the embodiment illustrated in FIG. 1, the shapes 10, 11 are a fictional sports apparel or equipment manufacturer's or distributor's logo (10) and a reverse image of the logo (11), although the logo itself (10), rather than the reverse image (11), may be provided under both eyes 14, 15.

Figure 8:
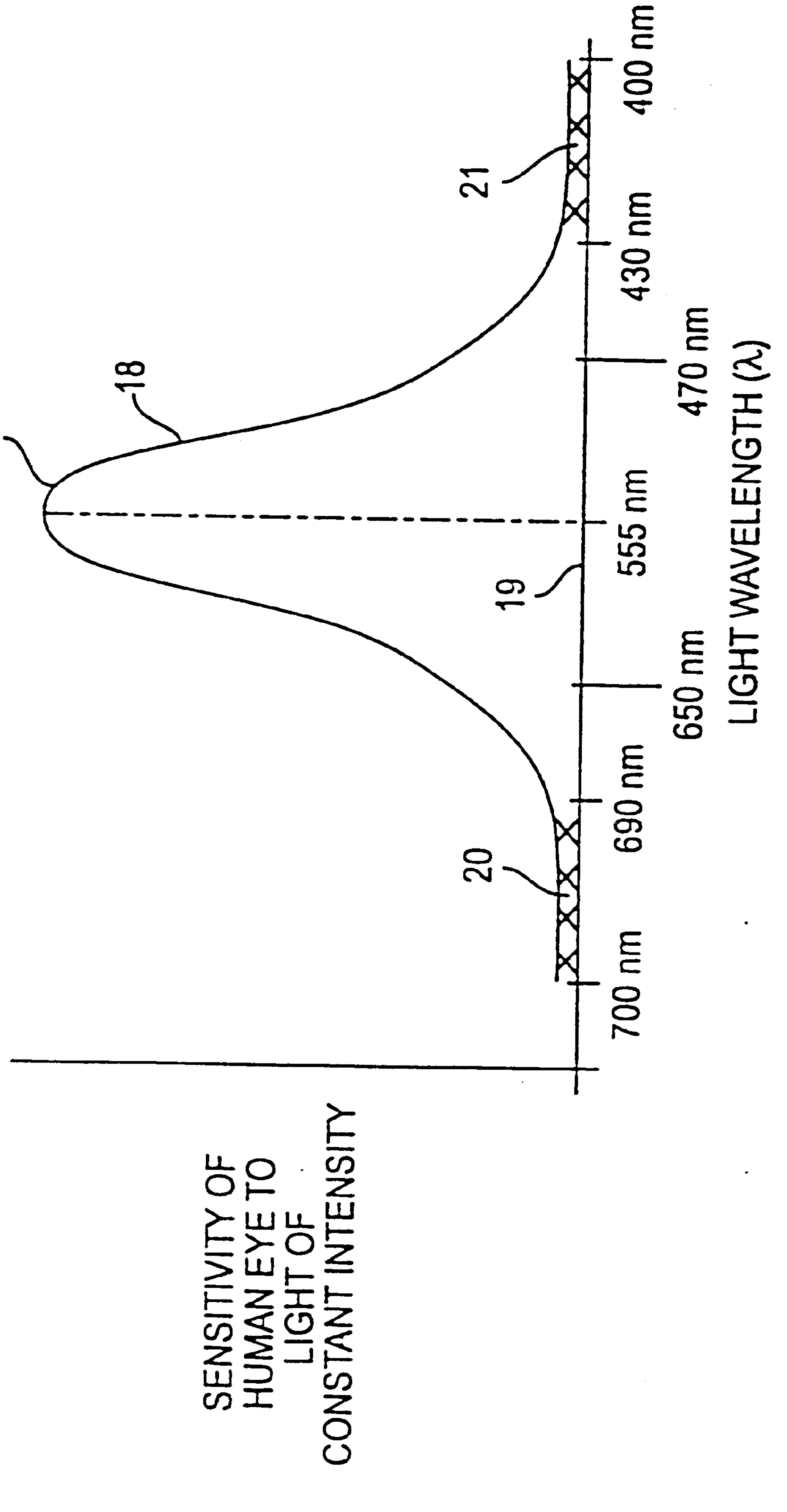
FIG. 8 is a schematic graphical representation of the sensitivity a human's eyes to light of constant intensity plotted against light wavelength.

The shapes 10, 11 are of a non-toxic material (although care still must be taken not to get the material or any component thereof into the eyes 14, 15 since at least temporary discomfort will result) having a non-reflective colored and finished exterior. The non-reflective colored and finished exterior preferably has characteristics comparable to conventional eye black (typically a mixture and gel of semi-solid form of Vaseline, lanolin, ceresin wax, beeswax, carnauba wax, and black oxide of iron C177499UV). That is it is dull or matte, rather than shiny or glossy, and is black and/or of other non-reflective colors. With particular reference to FIG. 8 which is a schematic graphical representation of the sensitivity of the human eye for light of constant intensity (plotted on the Y axis) versus light wavelength (plotted on the X axis) for the range of human visibility, typically the colors utilized according to the invention for the exterior of the shapes 10, 11 comprise colors having a wavelength greater than about 650 nm (middle of red) and less than about 470 nm (all of blue and violet), and preferably greater than about 690 nm and less than about 430 nm. The full range of human sensitivity is not well defined, varying from person to person, because—as illustrated in FIG. 8—the eye sensitivity curve 18 approaches the zero sensitivity line (X axis) 19 asymptotically. Typical limits include about 700 nanometers (nm) for red and about 400 nanometers for violet. The approximate values 690 nanometers and 430 nanometers, which define the shaded areas 20.

21 in FIG. 8, are provided where eye sensitivity has dropped to one percent of the maximum value at point 22 (typically at about 555 nm). The colors in area 20 range from deep reds to blacks while the colors in area 21 range from deep violets to blacks.

While it is highly preferable for maximum utility of the shapes 10, 11 that no colors except as described above are provided, where functionality can be compromised slightly, or where functionality is not the primary purpose for utilizing the shapes 10, 11, some white or brighter colors can be utilized to provide demarcation, or less than the entire conventional reflective area on the cheeks 12, 13 under the eyes 14, 15 may be covered by the shapes 10, 11. However in no case should shiny or glossy exterior surfaces of the shapes 10, 11 be provided, nor should large or continuous areas of white or bright colors.

Figure 2:
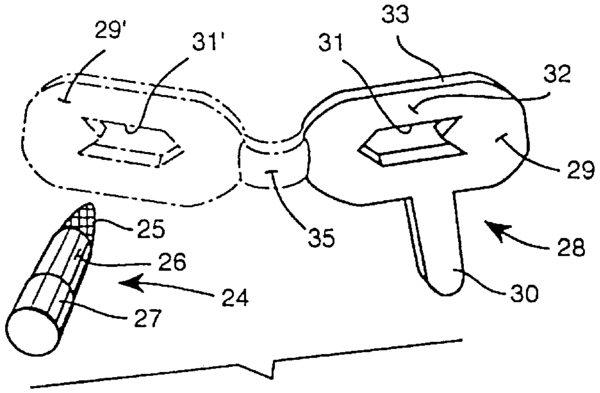
FIG. 2 is a schematic perspective view showing an exemplary stencil, and eye black marker, that can be used to apply the logo illustrated in FIG. 1.

FIG. 2 illustrates apparatus that may be utilized in the practice of the method of the present invention. A conventional eye black marker 24, having a stick of eye black 25 that is movable in and out of the conventional lipstick style container 26 by rotation of the end portion 27 thereof is provided for use in association with a stencil or mask 28. The stencil or mask assembly 28 may comprise a simple stencil 29, e.g. having an extension 30 for easy gripping by the user, and having a cut out 31 formed therein corresponding to the shape 10 or the shape 11. The stencil 29 may also have a centering mark 32 thereon for centering the cut out 31 underneath an eye 14, 15, and the spacing between the top edge 33 of the stencil and the first portion of the cut out 31 may be dimensioned so that the top edge 33 is placed underneath the eye 14, 15 during use so that the cut out 31 is at a position whereby eye black 25 may be safely and functionally applied on the cheek 12 or 13. If desired, instead of a simple stencil 29 the stencil assembly 28 may also include a nose piece 35 and a second stencil 29' on the opposite side of the nose piece 35 from the stencil 29. The cut out 31' provided therein (which is either identical to the cut out 31 or the reverse thereof) so that both cheeks 12, 13 can be done at the same time.

The eye black 25, when it is desired to be removed (e.g. typically a few minutes after an athletic contest, and certainly within a few hours after), is removed in the same manner that eye black is conventionally removed. That is it may be wiped off, washed off with soap and water, or both.

Figure 3:
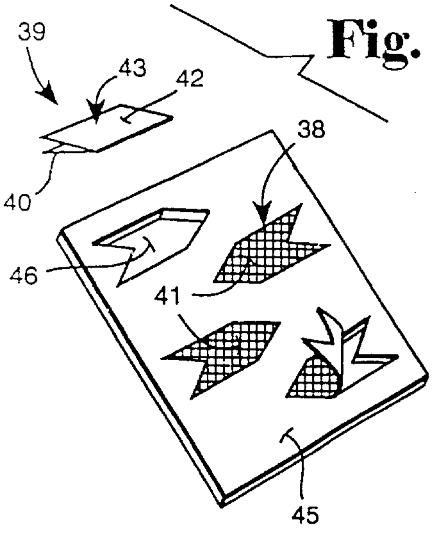
FIG. 3 is a schematic perspective view of exemplary decals that may be utilized according to the present invention co apply the logos illustrated in FIG. 1.

FIG. 3 illustrates alternative products that may be utilized to practice the method of the present invention, which products are also an aspect of the present invention. The products of FIG. 3 comprise decals 38, 39 of basically conventional construction (e.g. such as shown in U.S. Pat. Nos. 3,898,357 or 4,522,864) which comprise a substrate having a top face 41 and a bottom face 42. The bottom face 42 has a pressure sensitive adhesive thereon as illustrated schematically at 43 in FIG. 3, while the top face 41 comprises an exterior surface (during use) of a non-reflective colored and finished material described earlier. That is—as illustrated in FIG. 3—the surface 41 may be solid dull black, with or without lettering. As is conventional, the decals 38, 39 can be peeled off a supporting sheet assembly 45 from which the decals 38, 39 have been die-cut, being held in place before use with the adhesive 43 in contact with a release sheet 46 comprising the bottom substrate of the sheet assembly 45. The decals 38, 39 are applied merely by pressing them with the pressure sensitive adhesive 43 into contact with the cheeks 12, 13 so that they are held in place against the skin by the adhesive 43. To remove them one need simply peel off part of an edge of one of the decals 38, 39 from the skin, and pull.

Figure 4:
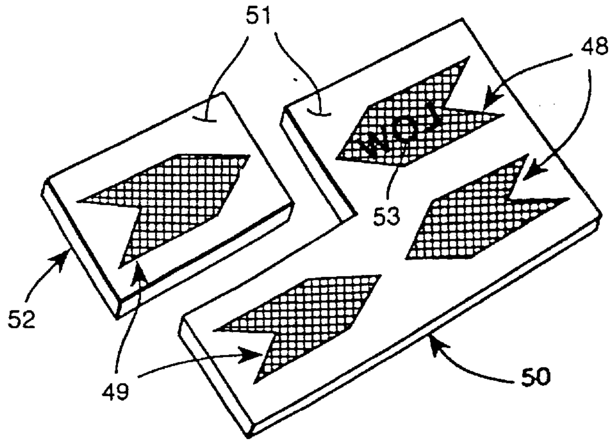
FIG. 4 is a view like that of FIG. 3 only showing temporary tattoos.

FIG. 4 illustrates other products according to the present invention utilizable in practicing the method of the present invention. In FIG. 4 conventional temporary tattoos 48, 49 are illustrated, the tattoos having the shapes 10, 11. The temporary tattoos 48, 49 are provided on a substrate 50, i.e. on top face 51 thereof, and are the reverse of the clearly demarcated geometric shape desired. That is the temporary tattoos 48 will provide the shapes 11 and the temporary tattoos 49 the shapes 10. As is conventional for the use of temporary tattoos, a section of the substrate 50 containing one of the tattoos (49) is cut out from the rest of the substrate 50, as illustrated for the cut out portion 52 in FIG. 4. After the cheek 12 to which it is applied has been cleaned so that it is free of oils, dirt, etc. the temporary tattoo 49 is put on the cheek 12, the bottom face (not shown) of the substrate 50 is wet (typically with water) and the substrate section 52 is pressed on so that the temporary tattoo 49 is in contact with the cheek 12 a sufficient time for the temporary tattoo 49 to adhere to the cheek, at which point the substrate portion 52 is slid off from the temporary tattoo 49 which adheres to the cheek 12. While conventional temporary tattoos last about three to five days, in most circumstances according to the invention it will be desirable to remove the temporary tattoo 48, 49 shortly after an athletic contest. Removal may be accomplished, as is conventional, using rubbing alcohol or baby oil which is applied and rubbed on the tattoo 48, 49, or by using pressure sensitive adhesive tape, the adhesive on the tape being applied to the temporary tattoo 48, 49 and being removed when the tape is removed.

FIG. 4 also illustrates for the upper of the temporary tattoos 48 another embodiment according to the invention. In this embodiment words are provided within the tattoo 48. The words—in the embodiment illustrated in FIG. 4 the single word "Low" which is a fictional name of a sports apparel or equipment manufacturer or distributor, such as a sports shoe manufacturer—is provided within the logo of that same manufacturer or distributor, as illustrated at 53. The word "Low" is illustrated in reverse in FIG. 4 since when it is applied as the shape 11 the letters will be mirror image. In order to maintain optimum functionality of the temporary tattoo 48 for preventing reflection of light into the human's eyes, the letters making up the word 53 are preferably of a red or a blue or violet, or there are red or blue or violet demarcation lines between it and the black of the body of the tattoo 48. Where optimum functionality is not critical, however, the word 53 may be of a clearer contrasting color to black than red or blue or violet, or it may have demarcation lines around the word 53 of a clearer contrasting color.

Figure 5:
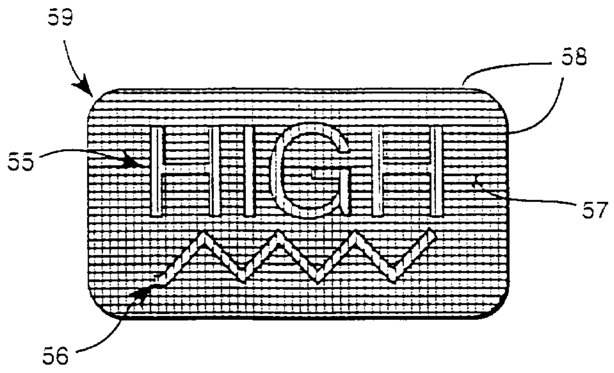
FIG. 5 is another exemplary form that the predefined clearly demarcated geometric shape according to the invention can take.

FIG. 5 illustrates another exemplary construction according to the invention. In this construction a decal is illustrated (although it could as easily be a tattoo, or even possibly a stencil image depending upon the details of what is illustrated therein). In this case clearly demarcated predefined geometric shapes are formed of a fictional sports apparel or equipment manufacturer's or distributor's name 55 and logo 56, within a primarily black or dark color surrounding area 57, also having predefined borders 58. The letters 55 and logo 56 are sized so as to comply with regulations of any regulatory body which oversees the athletic contest in which a participant utilizing the decal 59 will be participating (typically as a player or referee). For example if the contest is an NCAA sanctioned contest then the words 55 and logo 56 must fit within an area that is one and one-half inch square. Where optimum functionality is desired, the letters 55 and logo 56, or any demarcation between them and the surrounding primarily black area 57, are of a dull or matte color having a wavelength greater than about 650 nm and less than about 470 nm (preferably greater than about 690 nm and less than about 430 nm). Where optimum functionality is not required, and/or where the areas covered by the elements 55, 56 are small enough or discontinuous enough, a clearer contrasting (to the black or dark colored area 57) color may be utilized.

Figure 6:
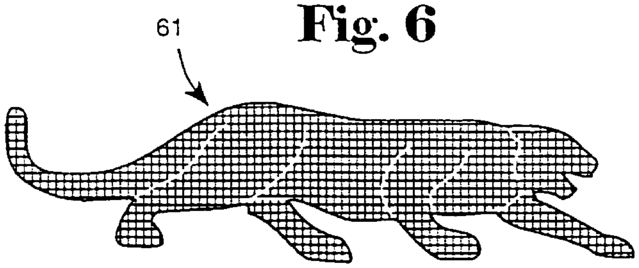
FIGS. 6 and 7 are views like that of FIG. 5 only for other embodiments according to the invention.
Figure 7:
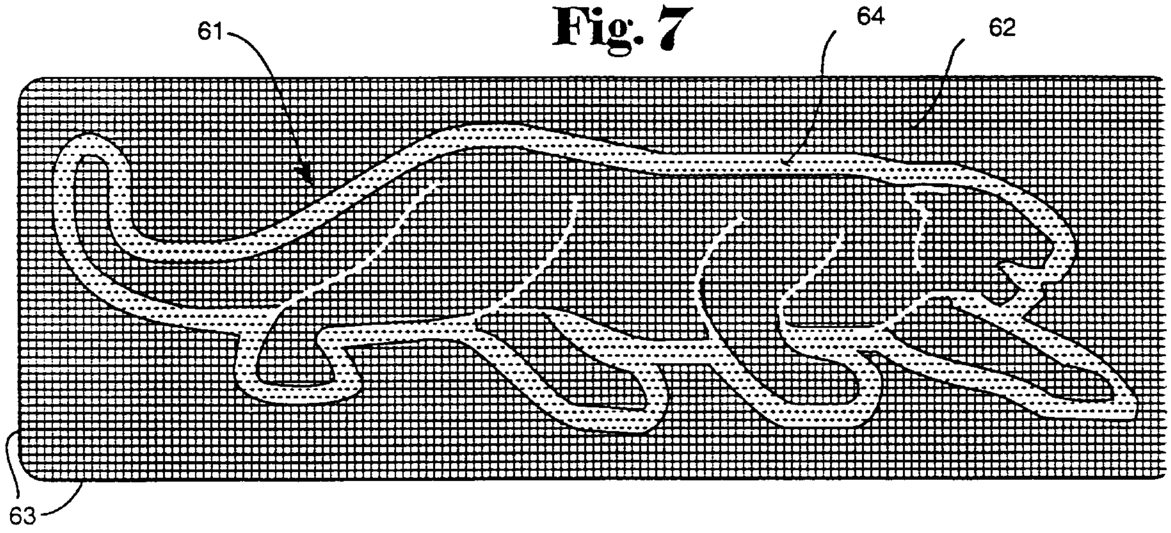

FIGS. 6 and 7 illustrate additional embodiments according to the invention. In FIG. 6 an exemplary team mascot—a black panther—is illustrated which may be stenciled on with eye black, or applied in decal or temporary tattoo form as long as the color thereof is dull or matte (not reflective). FIG. 7 illustrates the same mascot configuration 61 from FIG. 6 but within a surrounding background 62 having predefined clearly demarcated edges 63, with the mascot 61 demarcated from the surrounding black or dark colored area 62 by lines 64. The lines 64 preferably are a dull or matte color having a wavelength greater than about 690 nm and less than about 430 nm, but again where optimum functionality is not required may be of a clearer contrasting non-reflective color. The embodiment of FIG. 7 is typically more functional than the embodiment of FIG. 6 since the surrounding area 62 can be dimensioned for optimum functionality for minimizing light reflection into the user's eyes, whereas the mascot shape 61 per se may or may not properly cover the appropriate reflective portion of the cheeks 12, 13.

It will thus be seen that according to the present invention a highly advantageous yet simple method and products are provided for simultaneously reducing reflective light glare into a human's eyes from the human's cheeks while simultaneously providing a non-verbal communication to others. While the invention has been herein shown and described in what is presently conceived to be the most practical and preferred embodiment thereof it will be apparent to those of ordinary skill in the art that many modifications may be made thereof within the scope of the present invention, which scope is to be accorded the broadest interpretation of the appended claims so as to encompass all equivalent processes and products.

What is claimed is:

1. An apparatus for reducing reflected light glare into a human's eyes from the human's cheeks, the apparatus comprising:

a decal or a temporary tattoo having an exterior, when applied, surface comprising a non-reflective and non-toxic material of a dull or matte color having a wavelength falling outside of the range of wavelengths between 430 nm and 690 nm, the non-reflective material sufficient to substantially eliminate the reflection of incident light off the human's cheeks into the human's eyes; and a shape formed within the non-reflective material, the shape comprising a color contrasting with the dull or matte color, wherein the shape is configured to provide communication.

2. The apparatus of claim 1, wherein the shape is a manufacturer's or distributor's logo and/or name.

3. The apparatus of claim 1, wherein at least a portion of the shape has an exterior portion comprising the contrasting color and an interior portion comprising the dull or matte color.

4. The apparatus of claim 2, wherein an area encompassed within a periphery of the shape is no greater than 1½ square inches.

5. The apparatus of claim 1, further comprising an outline around a periphery of the shape.

6. The apparatus of claim 1, wherein the non-reflective material comprises a material having a wavelength falling outside of the range of wavelengths between 430 nm and 690 nm so as to absorb a substantial portion of light in the visible spectrum.

7. The apparatus of claim 1, wherein the apparatus is a decal comprising a substrate, wherein a bottom surface has a pressure sensitive adhesive thereon.

8. The apparatus of claim 1, wherein the apparatus comprises a temporary tattoo provided on a substrate, the temporary tattoo provided on a top face of the substrate.

9. The apparatus of claim 1, wherein the shape is a name, a mascot, or a logo of a school or of a team.

10. An apparatus for reducing reflected light glare into a human's eyes from the human's cheeks, the apparatus comprising:

a decal or a temporary tattoo having an exterior, when applied, surface comprising a nonreflective and non-toxic material of a dull or matte color having a wavelength falling outside of the range of wavelengths between 430 nm and 690 nm, the non-reflective material sufficient to substantially eliminate the reflection of incident light off the human's cheeks into the human's eyes; and the non-reflective material having a pre-defined shape, wherein the shape is a logo, a mascot, or a name of a school or of a team.

11. The apparatus of claim 10, wherein the pre-defined shape is formed within the non-reflective material, and has an interior portion formed from a color distinguishable from the dull or matte color.

12. The apparatus of claim 10, wherein the pre-defined shape is formed by a periphery of the non-reflective material.

* * * * *